US006821956B2

(12) United States Patent
Dzau et al.

(10) Patent No.: US 6,821,956 B2
(45) Date of Patent: Nov. 23, 2004

(54) THERAPEUTIC USE OF CIS-ELEMENT DECOYS IN VIVO

(75) Inventors: Victor J. Dzau, Los Altos Hills, CA (US); Gary H. Gibbons, Palo Alto, CA (US); Ryuichi Morishita, Palo Alto, CA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 09/839,752

(22) Filed: Apr. 19, 2001

(65) Prior Publication Data

US 2002/0052333 A1 May 2, 2002

Related U.S. Application Data

(63) Continuation of application No. 08/524,206, filed on Sep. 8, 1995, which is a continuation of application No. 08/144,717, filed on Oct. 29, 1993, now abandoned.

(51) Int. Cl.[7] .......................... A01N 43/04; C12P 21/06; C12N 5/00; C12N 15/88; C07H 21/04
(52) U.S. Cl. ........................ 514/44; 435/69.1; 435/375; 435/458; 536/23.1; 536/24.1; 536/24.5; 424/450
(58) Field of Search .......................... 514/44; 435/69.1, 435/375, 458, 172.3, 320.1; 536/23.1, 24.5, 24.1, 24.3, 24.33, 24.31; 424/450

(56) References Cited

U.S. PATENT DOCUMENTS

| | | | |
|---|---|---|---|
| 5,264,423 A | 11/1993 | Cohen et al. | |
| 5,276,019 A | 1/1994 | Cohen et al. | |
| 5,286,717 A | 2/1994 | Cohen et al. | |
| 5,631,237 A | 5/1997 | Dzau et al. | |
| 5,683,985 A | 11/1997 | Chu et al. | |
| 5,821,234 A | * 10/1998 | Dzau ........................... | 514/44 |
| 2003/0186922 A1 | * 10/2003 | Dzau et al. ................... | 514/44 |

FOREIGN PATENT DOCUMENTS

| | | |
|---|---|---|
| WO | WO 91/11535 | 8/1991 |
| WO | WO 92/18522 | 10/1992 |
| WO | WO 93/03770 | 4/1993 |
| WO | WO 93/14768 | 8/1993 |
| WO | WO 95/11684 | 4/1995 |
| WO | WO 95/11687 | * 5/1995 |

OTHER PUBLICATIONS

Kawauchi et al. Gene Therapy for Attenuating Cardiac Allograft Arteriopathy Using Ex Vivo E2F Decoy Transfection by HVJ–AVE–Liposome Method in Mice and Nonhuman Primates. Circulation Research 1063–1068, Nov. 24, 2000.*
Dzau et al. Fusigenic viral liposomes for gene therapy in cardiovascular diseases. PNAS (93), pp 11421–11425, Oct., 1996.*
Morishita et al., A gene therapy strategy using a transcription factor decoy of the E2F binding site inhibits smooth muscle cell proliferation in vivo. PNAS (92), pp 5855–5859 Jun. 1995.*
Mann et al., Ex–vivo gene therapy oif human casular bypass grafts with E2F decoy: the PREVENT single centre, randomised controlled trial. The Lancet (354), pp 1493–1498, Oct. 30, 1999.*
Barinaga et al., "Gene Therapy for Clogged Arteries Passes Test in Pigs," Science 265:738 (1994).
Bielinska et al., "Regulation of Gene Expression with Double–Stranded Phosphorothioate Oligonucleotides," Science 250:997–999 (1990).
Chien, "Molecular Advances in Cardiovascular Biology," Science 260:916–917 (1993).
Dalton, "Cell Cycle Regulation of the Human cdc2 Gene," The EMBO Journal 11(5):1979–1804 (1992).
Ebbecke et al., European Heart Journal 12:11 (1991).
Hiebert et al., "E1A–dependent Trans–activation of the Human Myc Promoter is Mediated by the E2f Factor," Proc. Natl. Acad. Sci. U. S. A. 86:3594–3598 (1989).
Hug et al., "Liposomes for the Transformation of Eukaryotic Cells," Biochem. Biophys. Acta 1097:1–17 (1991).
Hutchinson et al., Circulation 86:Suppl. I p. I –226 (1992).
Kaneda et al., "Increased Expression of DNA Cointroduced with Nuclear Protein in Adult Rat Liver," Science 243:375–378 (1989).
Libby et al., "A Cascade Model for Restenosis. A Special Case of Atheroscerosis Progression," Circulation 86:III–47–III–52 (1992).
Mannino et al., "Liposome Mediated Gene Transfer," BioTechniques 6:682–690 (1988).
Milligan et al., "Current Concepts in Antisense Drug Design," J. Med. Chem. 36:1923–1937 (1993).
Morishita et al., "In Vivo Gene Transfer into intact Blood Vessels: a Novel and Efficient Method," Circulation 86 (Suppl. I):1–227 (1992).

(List continued on next page.)

Primary Examiner—Gerry Leffers
Assistant Examiner—Maria Marvich
(74) Attorney, Agent, or Firm—Ginger R. Dreger; Heller Ehrman White & McAuliffe, LLP (57) ABSTRACT

The invention provides for the use of oligodeoxynucleotide decoys for the prophylactic or therapeutic treatment of diseases associated with the binding of endogenous transcription factors to genes involved in cell growth, differentiation and signalling or to viral genes. By inhibiting endogenous trans-activating factors from binding transcription regulatory regions, the decoys modulate gene expression and thereby regulating pathological processes including inflammation, intimal hyperplasia, angiogenesis, neoplasia, immune responses and viral infection. The decoys are administered in amounts and under conditions whereby binding of the endogenous transcription factor to the endogenous gene is effectively competitively inhibited without significant host toxicity. The subject compositions comprise the decoy molecules in a context which provides for pharmacokinetics sufficient for effective therapeutic use.

4 Claims, 7 Drawing Sheets

OTHER PUBLICATIONS

Mulligan et al., "The Basic Science of Gene Therapy," Science 260:926–932 (1993).

Nevins, "E2F: A Link Between the Rb Tumor Supressor Protein and Viral Oncoproteins," Science 258:424–429 (1992).

Ostrowski et al., "Glucocorticoid Regulation of Transcription at an Amplified, Episomal Promoter," Mol. Cell. Biol. 3:2045–2057 (1983).

Pagano et al., "Association of cdk2 Kinase with the Transcription Factor E2F During S Phase," Science 255:1144–1147 (1992).

Ritzenthaler et al., "Regulation of the $\alpha 1(I)$ Collagen Promoter via a Transforming Growth Factor–$\beta$ Activation Element," J. Biol. Chem. 268:13625–13631 (1993).

Ritzenthaler et al., "Transforming–growth–factor–$\beta$ Activation Elements in the Distal Promoter Regions of the Rat $\alpha 1$ Type I Collagen Gene," Biochem. J. 280:157–162 (1991).

Rubin et al., "Atherosclerosis in Mice: Getting to the Heart of a Polygenic Disorder." Trends in Genetics 10:199–204 (1994).

Schwartz et al., "Coronary Restenosis: Prospects for Solution and New Perspectives from a Porcine Model," Mayo Clinic Proceedings 68:54–62 (1993).

Stein et al., "Antisense Oligonucleotides as Therapeutic Agents—is the Bullet Really Magical?" Science 261:1004–12 (1993).

Sullenger et al., "Overexpression of TAR Sequences Renders Cells Resistant to Human Immunodeficiency Virus Replication," Cell 63:601–608 (1990).

Tomita et al., "Direct in Vivo Gene Introduction into Rat Kidney," Biochem. Biophys. Res. Comm. 186:129–134 (1992).

Tseng et al., "Antisense Oligonucleotide Technology in the Development of Caner Therapeutics," Cancer Gene Ther. 1:65–71 (1994).

Uhlmann et al., Chemical Reviews 90:543–584 (1990).

Weintraub et al., "Retinoblastoma Protein Switches the E2F Site from Positive to Negative Element," Nature 358:259–261 (1992).

Wu et al., "Inhibition of In Vitro Transcription by Specific Double–stranded Oligodeoxyribonucleotides," Gene 89:203–209 (1990).

Yee et al., "Promoter Interaction of the E1A–inducible Factor E2F and its Potential Role in the Formation of a Multi–component Complex," The EMBO Journal 6:2061–2068 (1987).

Chu et al., "The Stability of Different Forms of Double–stranded Decoy DNA in Serum and Nuclear Extracts," Nucleic Acids Research 20:5857–5858 (1992).

Eck et al., "Inhibition of Phorbol Ester–Induced Cellular Adhesion by Competitive Binding of NF–Kappa B In Vivo," Molecular and Cellular Biology 13:6530–6536 (1993).

Medford et al., "Inhibition of TNF–alpha Induced Vascular Cell Adhesion Molecule–1 Gene Expression in Human Vascular Endothelial and Smooth Cells Using Transcriptional Factor Decoys," Circulation, American Heart Association 88:177 (1993).

* cited by examiner

| Cis-element Transcription Factor | Cellular Process | Therapeutic Application |
|---|---|---|
| E2F | cell proliferation | neointimal hyperplasia, neoplasia, glomerulonephritis, angiogenesis, inflammation |
| AP-1 | cell growth, differentiation, growth factor expression | neointimal hyperplasia, cardiac myocyte growth/differentiation |
| NFκB | cytokine expression, leukocyte adhesion molecule expression, oxidant stress response, cAMP and protein kinase C activation, immunoglobulin expression | inflammation, immune response, transplant rejection, ischemia-reperfusion injury, glomerulonephritis |
| SSRE | response to shear stress: growth factor expression, vasoactive substances, matrix proteins, adhesion molecules | neointimal hyperplasia, bypass grafts, angiogenesis, collateral formation |
| CREB | cAMP response | cAMP activated events |
| MEF-2 | cardiac myocyte differentiation and hypertrophy | cardiac myocyte growth and differentiation |
| CArG box | cardiac myocyte differentiation | cardiac myocyte growth and differentiation |
| tax | viral replication | HTLV infection |
| VP16 | viral replication | Herpes infection |
| TAR/tat | viral replication | HIV infection |
| GRE/HRE MRE | glucocorticoid, mineralocorticoid induced events | steroid hormone processes, e.g., breast or prostate cell growth |
| Heat shock RE | heat shock response | cellular stresses, e.g., ischemia and hypoxia |
| SRE | growth factor responses | cell proliferation/differentiation |
| AP-2 | cAMP and protein kinase response, retinoic acid response | cell proliferation |
| sterol response element | modulation of LDL cholesterol receptor expression | hypercholesterolemia |
| TRE TGFβ responsive element | Transforming growth factor beta-induced cellular processes | cell growth, differentiation, migration, angiogenesis, intimal hyperplasia, matrix generation, apoptosis |

Figure 6

| INDICATION | ROUTE | VEHICLE | PLASMID/ OLIGONUCLEOTIDE |
|---|---|---|---|
| HIV infection | intravenous injection | gp160 in neutral liposomes | TAR containing oligonucleotide |
| solid tumor | intratumoral injection | tumor-specific antibody with liposomes | E2F |
| Inflammatory skin disease and dermatitis | topical | polymer | NFκB, E2F |
| Hypercholesterolemia | intravenous injection, portal vein injection | cationic liposomes asialoglycoprotein receptor targeting with liposomes | sterol responsive element to increase LDL receptors |
| vein bypass grafts | topical/intralumial | polymer, liposomes | E2F |
| glomerulonephritis | intravenous, intrarenal | polymer, liposomes | E2F, NFκB |
| myocardial infarction | intracoronary | liposomes, polymer | NFκB, E2F, AP-1 |
| organ transplant, e.g., cardiac/renal | intravascular, ex vivo | liposomes, polymer | NFκB |

SEQUENCE LISTING

```
<160> NUMBER OF SEQ ID NOS: 12

<210> SEQ ID NO 1
<211> LENGTH: 14
<212> TYPE: DNA
<213> ORGANISM: Homo sapiens

<400> SEQUENCE: 1
ctagatttcc cgcg                                                       14

<210> SEQ ID NO 2
<211> LENGTH: 14
<212> TYPE: DNA
<213> ORGANISM: Homo sapiens

<400> SEQUENCE: 2
gatccgcggg aaat                                                       14

<210> SEQ ID NO 3
<211> LENGTH: 14
```

```
<212> TYPE: DNA
<213> ORGANISM: Artificial Sequence
<220> FEATURE:
<223> OTHER INFORMATION: derived from Homo sapiens

<400> SEQUENCE: 3
ctagatttcg agcg                                                    14

<210> SEQ ID NO 4
<211> LENGTH: 14
<212> TYPE: DNA
<213> ORGANISM: Artificial Sequence
<220> FEATURE:
<223> OTHER INFORMATION: derived from Homo sapiens

<400> SEQUENCE: 4
gatccgctcg aaat                                                    14

<210> SEQ ID NO 5
<211> LENGTH: 30
<212> TYPE: DNA
<213> ORGANISM: Homo sapiens

<400> SEQUENCE: 5
gatcaaaagc gcgaatcaaa agcgcgaatc                                   30

<210> SEQ ID NO 6
<211> LENGTH: 30
<212> TYPE: DNA
<213> ORGANISM: Homo sapiens

<400> SEQUENCE: 6
gattcgcgct tttgattcgc gcttttgatc                                   30

<210> SEQ ID NO 7
<211> LENGTH: 30
<212> TYPE: DNA
<213> ORGANISM: Artificial Sequence
<220> FEATURE:
<223> OTHER INFORMATION: derived from Homo sapiens

<400> SEQUENCE: 7
gatcaaagaa ctgaatcaaa gaactgaatc                                   30

<210> SEQ ID NO 8
<211> LENGTH: 30
<212> TYPE: DNA
<213> ORGANISM: Artificial Sequence
<220> FEATURE:
<223> OTHER INFORMATION: derived from Homo sapiens

<400> SEQUENCE: 8
gattcagttc tttgattcag ttctttgatc                                   30

<210> SEQ ID NO 9
<211> LENGTH: 14
<212> TYPE: DNA
<213> ORGANISM: Artificial Sequence
<220> FEATURE:
<223> OTHER INFORMATION: derived from Homo sapiens

<400> SEQUENCE: 9
tccagcttcg tagc                                                    14

<210> SEQ ID NO 10
```

```
<211> LENGTH: 13
<212> TYPE: DNA
<213> ORGANISM: Artificial Sequence
<220> FEATURE:
<223> OTHER INFORMATION: derived from Homo sapiens

<400> SEQUENCE: 10
gctagctagg aag                                                          13

<210> SEQ ID NO 11
<211> LENGTH: 27
<212> TYPE: DNA
<213> ORGANISM: Homo saiens

<400> SEQUENCE: 11
gatcctgtac aggatgttct agctaca                                           27

<210> SEQ ID NO 12
<211> LENGTH: 27
<212> TYPE: DNA
<213> ORGANISM: Homo sapiens

<400> SEQUENCE: 12
tgtagctaga acatcctgta caggatc                                           27
```

THERAPEUTIC USE OF CIS-ELEMENT DECOYS IN VIVO

This application is a continuation of U.S. patent application Ser. No. 08/524,206 filed Sep. 8, 1995, which is a continuation of U.S. patent application Ser. No. 08/144,717 filed Oct. 29, 1993, now abandoned, from which applications priority is claimed under 35 U.S.C. §120.

TECHNICAL FIELD

The field of this invention is therapeutic treatment of disease with double stranded nucleic acids which bind transcription factors.

BACKGROUND

A wide variety of diseases result from the over- or under-expression of one or more genes. Given cells may make insufficient amounts of a protein (e.g. insulin) or too much of a protein, be it a normal protein (e.g. TNF), a mutant protein (e.g. an oncogene), or a non-host protein (e.g. HIV tat). The ultimate goal of therapeutic intervention in such diseases is a selective modulation of gene expression.

A variety of methods of transcriptional modulation in vitro have been reported including the use of anti-sense nucleic acids capable of binding nascent message, intracellular immunization with dominant negative mutants.

With the broad potential therapeutic applications, massive efforts have been extended by prominent laboratories and clinics around the world to extend these methods in vivo. To date, the transcription factor decoy strategy has never been successfully adopted in vivo.

RELEVANT LITERATURE

Description of the roles of transcription factors may be found in Nevins, *Science* 258, 424–429 (1992); Dalton, *EMBO J.* 11, 11797 (1992); Yee et al. ibid. 6, 2061 (1987), Weintraub et al., *Nature* 358, 259–261 (1992), Pagano et al., *Science* 255, 1144–1147 (1992). Viral coat protein-liposome mediated transfection is described by Kaneda et al., *Science* 243, 375 (1989). Ritzenthaler et al. (1991) *Biochem J.* 280, 157–162; Ritzenthaler et al (1993) *J Biol Chem* 268, 13625–13631; Bielinska et al., *Science* 16, 997–1000 (1990) and Sullenger et al., *Cell* 63, 601–608 (1990) describe inhibition of transcription with double stranded nucleic acids.

A general discussion concerning the mechanism of restenosis may be found in Libby et al., *Circulation* 86, III-47 (1992) and Clowes et al., *J. Cardiovasc. Pharmacol.* 14, S12–15 (1989).

SUMMARY OF THE INVENTION

The invention provides for the therapeutic treatment of diseases associated with the binding of endogenous transcription factors to genes involved in cell growth, differentiation and signalling or to viral genes. Methods and compositions are provided for blocking the capacity of endogenous trans-activating factors to modulate gene expression and thereby regulating pathological processes including inflammation, intimal hyperplasia, angiogenesis, neoplasia, immune responses and viral infection.

The methods comprise administering to a patient double stranded nucleic acid "decoys" in a form such that the decoys are capable of entering target cells of the patient and specifically binding an endogenous transcription factor, thereby competitively inhibiting the transcription factor from binding to an endogenous gene. The decoys are administered in amounts and under conditions whereby binding of the endogenous transcription factor to the endogenous gene is effectively competitively inhibited without significant host toxicity. Depending on the transcription factor, the methods can effect up- or down-regulation of gene expression. The subject compositions comprise the decoy molecules in a context which provides for pharmacokinetics sufficient for effective therapeutic use.

BRIEF DESCRIPTION OF THE FIGURES

FIGS. 1. A–C Effect of NRE "decoy" on renin gene expression in cultured SMG cells. SCA-9 cells expressed renin as shown by immunohistochemistry (panel A). Primer extension analysis demonstrated that this was exclusively Ren 2 (panel B). These cells effectively took up FITC labeled double stranded decoy oligomer corresponding to the NRE (panel C). RNA was prepared 24 hours after transfection from control and "decoy" treated SCA-9 cells. Note that Ren 1 mRNA could be observed after exposure of the cells to the NRE decoy (panel B, lane 4).

FIG. 2. Detection of the NRE binding protein in cultured SMG cells. Nuclear extracts were prepared from SCA-9 cells and incubated with 32P end-labeled mouse renin NRE oligonucleotide. Competition analysis was performed with 50- and 100-fold excess of unlabeled NRE oligonucleotide. Note that a specific NRE:NRE binding protein complex formation was observed.

FIG. 3. In Vivo Expression of CAT in the Mouse SMG. Ten ug of renin gene CAT construct was transfected directly into the SMG of DBA/2J mice using the HVJ-DNA-Liposome technique. Four days after transfection, the SMG was removed, cell extracts prepared and CAT activity measured.

FIG. 4. Schematic diagram of the factors influencing renin gene expression. The hatched bar represents the CRE/NRE region present in the renin gene. The CRE binding protein and the NRE binding protein compete for binding to this region. The triangle represents the 150 base pair insert which is present in the Ren 2 gene.
Ren 1 expression: in the kidney, the CRE binding protein binds tighter, blocking the binding of the NRE binding protein, and allowing expression of the Ren 1 gene. In the SMG, an inhibitory protein forms an inactive complex with the CRE binding protein, allowing the NRE binding protein to bind, silencing expression of Ren 1.
Ren 2 expression: The 150 bp insertion interferes with the NRE function in the Ren 2 gene, resulting in Ren 2 expression in the SMG and kidney.

FIG. 5. Table of exemplary transcription factors and related cis elements, the cellular processes impacted, and therapeutic indications.

DESCRIPTION OF SPECIFIC EMBODIMENTS

Methods and compositions are provided for modulating gene expression in vivo. The methods involve administering a composition to a patient so as to introduce into a target cell molecular decoys comprising double-stranded nucleic acid, usually DNA, to which transcription factors endogenous to the target cell bind. Various methods are employed for in vivo administration of the decoys such that sufficient decoys enter into the target cells to competitively inhibit transcription factor binding to an endogenous gene regulatory region.

The compositions which are employed comprise "decoys": double-stranded nucleic acid molecules with high binding affinity for the targeted transcription factors. The targeted transcription factors are endogenous, sequence-specific double-stranded DNA binding proteins which modulate (increase or decrease) the rate of transcription of one or more specific genes in the target cell. Essentially any such transcription factor (henceforth, "transcription factor") can be targeted so long as a specific decoy capable of competitively inhibiting binding to the endogenous gene can be identified. Numerous transcription factors and their binding sequences are known in the art as are methods for identifying such complements, see e.g. Wang and Reed (1993) Nature 364, 121 and Wilson et al. (1991) Science 252, 1296. As used herein, endogenous means that the gene or transcription factor is present in the target cell at the time the decoy is introduced.

The transcription factors will, for the most part and depending on the clinical indication, regulate the transcription of genes associated with cell growth, differentiation and signalling or viral genes resident in the target cell. Examples include genes necessary for mitosis, particularly going from $G_o$ to S, such as proteins associated with check points in the proliferative cycle, cyclins, cyclin dependent kinases, proteins associated with complexes, where the cyclin or cdk is part of the complex, Rosenblatt et al., *Proc. Natl. Acad. Sci.* 89, 2824 (1992) and Pagano et al., *Science* 255, 1144 (1992). Often such genes or the transcription factors themselves will be oncogene products or cellular counterparts, e.g. fos, jun, myc, etc. Other examples include genes encoding secreted proteins and peptides such as hormones e.g. growth factors, cytokines, e.g. interleukins, clotting factors, etc. Target transcription factors also include host and host-cell resident viral transcription factors which activate viral genes present in infected host cells.

Preferred target transcription factors are activated (i.e. made available in a form capable of binding DNA) in a limited number of specifically activated cells. For example, a stimulus such as a wound, allergen, infection, etc may activate a metabolic pathway that is triggered by the transient availability of one or more transcription factors. Such transcription factors may be made available by a variety of mechanisms such as release from sequestering agents or inhibitors (e.g. NFκB bound to IκB), activation by enzymes such as kinases, translation of sequestered message, etc. Desirably, the target transcription factor(s) will be associated with genes other than genes whose lack of expression results in cytotoxicity. For the most part, it is desirable not to kill the cell, but rather to inhibit or activate specific gene transcription.

Exemplary transcription factors and related cis elements, the cellular processes impacted, and therapeutic indications include those listed in FIG. 5.

| Cis-elemnt Txn Factor | Cellular Process | Therapeutic Application |
| --- | --- | --- |
| E2F | cell proliferation | neointimal hyperplasia, neoplasia glomerulonephritis, angiogenesis, inflammation |
| AP-1 | cell growth, differentiation, growth factor expression | neointimal hyperplasia, cardiac myocyte growth/differentiation |
| NFkB | cytokine expression, leukocyte adhesion molecule expression, oxidant stress response, cAMP and protein kinase C activation, Ig expression | inflammation, immune response, transplant rejection, ischemia-reperfusion injury, glomerulonephritis |

-continued

| Cis-elemnt Txn Factor | Cellular Process | Therapeutic Application |
| --- | --- | --- |
| SSRE | response to shear stress: growth factor expression vasoactive substances, matrix proteins, adhesion molecules. | neointimal hyperplasia, bypass grafts, angiogenesis, collateral formation. |
| CREB | cAMP response | cAMP activated events |
| MEF-2 | cardiac myocyte differentiation and hypertrophy | cardiac myocyte differentiation and growth. |
| CArG box | cardiac myocyte differentiation | cardiac myocyte growth and differentiation. |
| tax | viral replication | HTLV infection |
| VP16 | viral replication | Herpes infection |
| TAR/tat | viral replication | HIV infection |
| GRE/HRE MRE | glucocorticoid, mineralocorticoid induced events | steroid hormone processes e.g. (breast or prostate cell growth). |
| Heat shock RE | heat shock response | cellular stresses e.g. ischemia, hypoxia |
| SRE | growth factor responses | cell proliferation/differentiation |
| AP-2 | cAMP and protein kinase response, retinoic acid response | cell proliferation. |
| sterol response element | modulation of LDL cholesterol receptor expression | hypercholesterolemia |
| TRE TGFb responsive element | Transforming growth factor beta induced cellular processes | cell growth, differentiation, migration, angiogenesis, intimal hyperplasia, matrix generation, apoptosis. |

The length, structure and nucleotide sequence of the decoy will vary depending on the targeted transcription factor, the indication, route of administration, etc. For example, targeted transcription factors frequently bind with different degrees of affinity to a variety of sequences, normally sharing a high degree of homology. Accordingly, one may choose to use a sequence associated with a particular target gene or use a consensus sequence based on the nucleotide at each site which occurs most frequently in the binding sequences to which the particular transcription factor binds. For example, when targeting a host transcription factor involved in viral transcription, it may be possible to minimize undesirable effects on host transcriptions preferable by employing the viral-specific binding sequence. Similarly, where transcription is mediated by a multimeric complex, it is often desirable to target a single transcription factor to minimize effects on non-targeted genes. For example, in the case of Herpes virus transcription, one may target the viral VP16 without concomitant targeting of the promiscuous host Oct protein.

In addition to binding affinity, the decoys are also selected for binding specificity. Desirably, the decoys will be highly specific for the target transcription factor(s) such that their effect on nontarget cells and nontargeted metabolic processes of target cells are minimized. Such selection is accomplished in vitro by comparative binding to known transcription factors and nuclear extracts and in culture and in vivo by assaying nontargeted cell function and effects on nontargeted cell types.

The decoys contain sufficient nucleotide sequence to ensure target transcription factor binding specificity and affinity sufficient for therapeutic effectiveness. For the most part, the target transcription factors will require at least six base pairs, usually at least about eight base pairs for sufficient binding specificity and affinity. Frequently, providing the decoys with flanking sequences (ranging from about 5 to 50 bp) beside the binding site enhance binding affinity and/or specificity. Accordingly, cis element flanking regions may be present and concatemer oligonucleotides may be constructed with serial repetitions of the binding and/or cis element flanking sequences.

In one embodiment, the decoys are non-replicative oligonucleotides fewer than 100 bp, usually fewer than 50 bp and usually free of coding sequence, being primarily from the non-coding 5' region of a gene. Alternatively, the decoys may comprise a portion of a larger plasmid, including viral vectors, capable of episomal maintenance or constitutive replication in the target cell to provide longer term or enhanced intracellular exposure to the decoy sequence. Plasmids are selected based on compatibility with the target cell, size and restriction sites, replicative frequency, copy number maintenance, etc. For example, plasmids with relatively short half-lives in the target cell are preferred in situations where it is desirable to maintain therapeutic transcriptional modulation for less than the lifetime of the target cell. Exemplary plasmids include pUC expression vectors driven by a beta-actin promoter and CMV enhancer, vectors containing elements derived from RSV or SV40 enhancers, etc. The adeno-associated viral vector preferentially integrates in chromosome 19 and may be utilized for longer term expression.

The oligonucleotides which are employed may be naturally occurring or other than naturally occurring, where the synthetic nucleotides may be modified in a wide variety of ways, see e.g. Bielinska et al (1990) Science 250, 997. Thus, oxygens may be substituted with nitrogen, sulfur or carbon; phosphorus substituted with carbon; deoxyribose substituted with other sugars, or individual bases substituted with an unnatural base. In each case, any change will be evaluated as to the effect of the modification on the binding of the oligonucleotide to the target transcription factor, as well as any deleterious physiological effects. These modifications have found wide application for "anti-sense" oligonucleotides, so that their safety and retention of binding affinity are well established in the literature. See, for example, Wagner et al., Science 260, 1510–1513 (1993). The strands may be synthesized in accordance with conventional ways using phosphoramidite synthesis, commercially available automatic synthesizes, and the like.

The administered compositions may comprise individual or mixtures of decoys. Usually the mixture will not exceed 4 different decoys usually not exceed 2. The decoys are administered to a host in a form permitting cellular internalization of the decoys in an amount sufficient to competitively inhibit the binding of the targeted transcription factor to an endogenous gene. The host is typically a mammal, usually a human. The selected method of administration depends principally upon the target cell, the nature of the decoy, the host, the size of the decoy. Exemplary methods are described in the examples below; additional methods including transfection with a retrovirus, viral coat protein-liposome mediated transfection, lipofectin etc. are described in Dzau et al., Trends in Biotech 11, 205–210 (1993).

Where administered in liposomes, the decoy concentration in the lumen will generally be in the range of about 0.1 uM to 50 uM per decoy, more usually about 1 uM to 10 uM, most usually about 3 uM. For other techniques, usually one will determine the application rate empirically, using conventional techniques to determine desired ranges.

In some situations it may be desirable to provide the decoy source with an agent which targets the target cells, such as an antibody specific for a surface membrane protein on the target cell, a ligand for a receptor on the target cell, etc. For example, for intervention in HIV infection, cells expressing HIV gene products or CD4 may be specifically targeted with gene product or CD4-specific binding compounds. Also, where liposomes are involved, one may wish to include proteins associated with endocytosis, where the proteins bind to a surface membrane protein associated with endocytosis. Thus, one may use capsid proteins or fragments thereof tropic for a particular cell type, antibodies for proteins which undergo internalization in cycling, proteins that target intracellular localization and enhance intracellular half-life.

The application of the subject therapeutics are preferably local, so as to be restricted to a histological site of interest e.g. localized inflammation, neoplasia or infection. Various techniques can be used for providing the subject compositions at the site of interest, such as injection, use of catheters, trocars, projectiles, pluronic gel, stents, sustained drug release polymers or other device which provides for internal access, or the like. Where an organ or tissue is accessible because of removal from the patient, such organ or tissue may be bathed in a medium containing the subject compositions, the subject compositions may be painted onto the organ, or may be applied in any convenient way. Alternatively, systemic administration of the decoy using e.g. lipofection, liposomes with tissue targeting (e.g. antibody), etc. may be practiced. Systemic administration is most applicable where the distribution of the targeted transcription factor is primarily limited to targeted cell types, e.g. virus-specific transcription factors limited to infected cells, mutant oncogenic transcription factors limited to transformed cells, etc.

Optimal treatment parameters will vary with the indication, decoy, clinical status, etc., and are generally determined empirically, using guidance provided herein. Several exemplary indications, routes, vehicles of administration, and decoy combinations are disclosed in FIG. 6.

Figure 6:
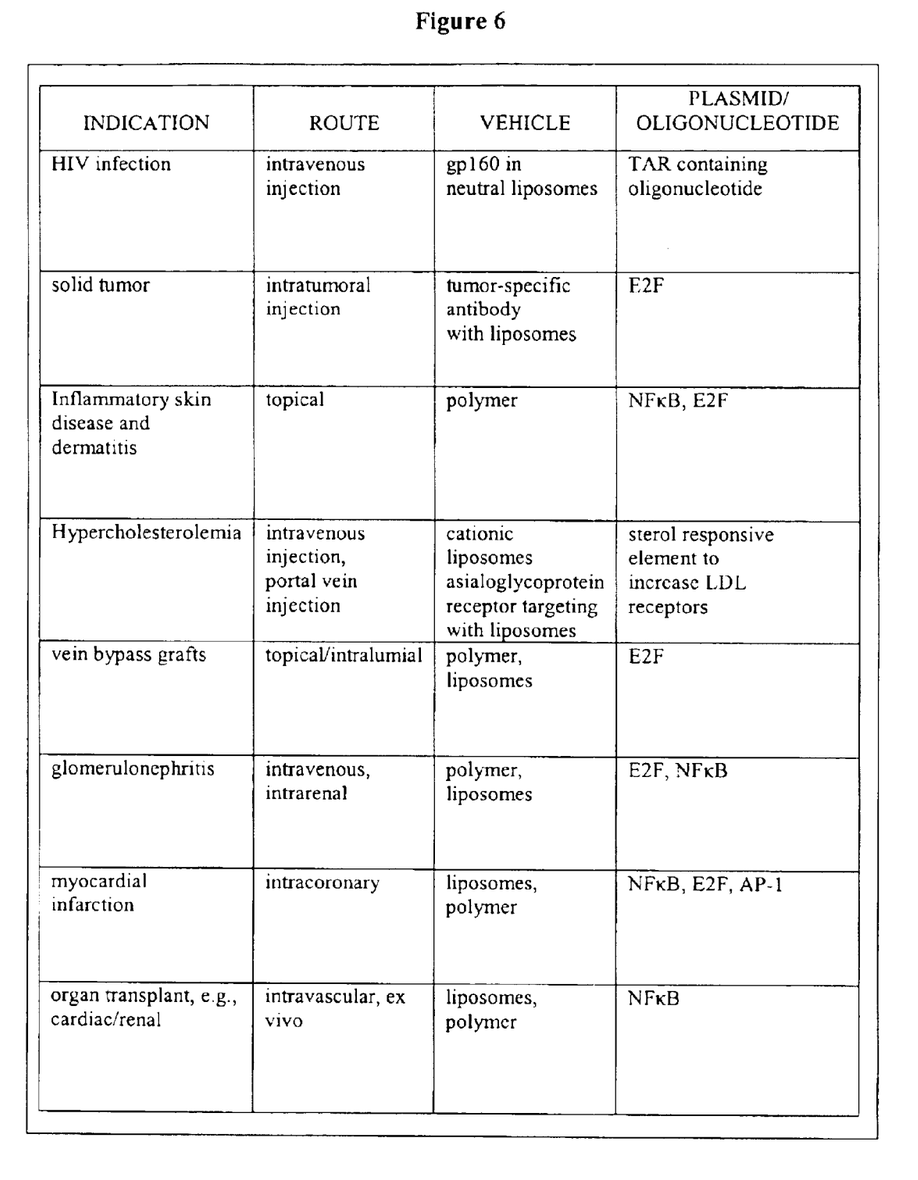
FIG. 6. Table of exemplary indications, routes, vehicles for administration, and decoy combinations.

| INDICATION | ROUTE | VEHICLE | PLASMD/ OLIGO |
| --- | --- | --- | --- |
| HIV infection | intravenous inj. | gp160 in neutral liposomes | TAR containing oligo |
| solid tumor | intratumoral inj. | tumor-specific Ab with liposomes | E2F |
| Inflammatory skin disease and dermatitis | topical | polymer | NFκB, E2F |
| Hypercholesterolemia | intravenous inj. portal vein inj. | cationic liposomes asialoglycoprotein receptor targeting with lipsomes | sterol responsive element to increase LDL receptors |
| vein bypass grafts | topical/ intralumina l | polymer, liposomes | E2F |
| glomerulonephritis | intravenous, intrarenal | polymer, liposomes | E2F, NFκB |
| myocardial infarction | intracoronary | liposomes, polymer | NFκB, E2F, AP-1 |
| organ transplant esp. cardiac/renal | intra- vascular, ex vivo | liposomes, polymer | NFκB |

A wide variety of indications may be treated, either prophylactically or therapeutically with the subject compositions. For example, prophylactic treatment may inhibit mitosis or proliferation or inflammatory reaction prior to a stimulus which would otherwise activate proliferation or inflammatory response, where the extent of proliferation and cellular migration may be undesirable. Similarly, a therapeutic application is provided by a situation where proliferation or the inflammatory response is about to be initiated or has already been initiated and is to be controlled. The methods and compositions find use, particularly in acute situations, where the number of administrations and time for administration is relatively limited.

Conditions for treatment include such conditions as neoproliferative diseases including inflammatory disease states, where endothelial cells, inflammatory cells, glomerular cells may be involved, restenosis, where vascular smooth muscle cells are involved, myocardial infarction, where heart muscle cells may be involved, glomerular nephritis, where kidney cells are involved, hypersensitivity such as transplant rejection where hematopoietic cells may be involved, cell activation resulting in enhancement of expression of adhesion molecules where leukocytes are recruited, or the like. By administering the decoys to the organ ex vivo prior to implantation and/or after implantation, upregulation of the adhesion molecules may be inhibited. Adhesion molecules include homing receptors, addressing, integrins, selecting, and the like.

The following examples are offered by way of illustration and not by way of limitation.

EXPERIMENTAL

EXAMPLE 1

Transfection of E2F Decoys into Cultured Cells

For the nuclear extracts, vascular smooth muscle cells ("VSMCs") were stimulated by serum until confluent. After confluent, the cells were made quiescent by placing in serum free medium for 48 h. After the transfection of decoy oligodeoxynucleotides ("ODN"; 14 bp) essentially as described in Morishita et al. (1993) Proc. Natl. Acad. Sci. USA, 90, 8474–8478, cells were stimulated by 5% serum. After 6 h, RNA was extracted by RNAzol (Tel-Test Inc, Texas) Chomczynski and Sacchi (1987) Anal Biochem 162, 156–159. Levels of PCNA, cdc2 and beta-actin mRNAs were measured by RT-PCR (Morishita et al. (1993) supra). The PCNA primer (nucleotides 150–177 of rat PCNA cDNA) and the cdc2 5' primer (nucleotides 54–75 of human cdc2 cDNA) were previously described (Morishita et al. (1993) supra). The primers complementary to the rat beta-actin gene were obtained from Clontech Laboratories Inc. (Palo Alto, Calif.). Aliquots of RNA were amplified simultaneously by PCR (30 cycles) and compared with a negative control (primers without RNA). Amplification products were electrophoresed through 2% agarose gels stained with ethidium bromide. A gel mobility shift assay was performed as previously described (Horiuchi et al., J. Biol. Chem. 266, 16247–16254 (1991).

The 14 bp double-strand ODN effectively abolished the binding of the E2F transcription factor to a specific binding site in serum stimulated VSMCs. See also, Hiebert et al. (1989) PNAS 86, 3594. Transfection of the E2F decoy ODN markedly inhibited the induction of c-myc, cdc2 and PCNA mRNA expression in response to serum stimulation. The E2F decoy ODN had no effect on beta-actin mRNA expression. Furthermore, the control missense E2F element ODN containing two base pair substitutions that eliminate E2F binding failed to inhibit the induction of c-myc, cdc2 and PCNA RNA expression in response to serum stimulation. In association with effective inhibition of cell cycle regulatory gene expression, transfection of the 14 bp E2F decoy also abolished serum-stimulated VSMC proliferation. In contrast, the missense E2F element ODN had no effect on mitogenesis induced by serum.

To further confirm the specificity of this response to the E2F decoy, a 30 bp double-stranded ODN which contained two 8 base pair E2F cis elements capable of specific binding to E2F was employed (Weintraub et al., Nature 358, 259–261 (1992)). In the 30 bp E2F decoy the fifth nucleotide of the 8 bp E2F cis elements was changed from C to G. Despite these differences in flanking sequences and nucleotide composition, both E2F decoys effectively bind E2F and inhibit serum-stimulated vascular smooth muscle cell (VSMC) proliferation. Moreover, a 30 bp missense E2F element ODN with 5 bp substitutions with the 8 bp E2F consensus elements fails to bind E2F and also fails to inhibit serum-stimulated VSMC proliferation. Thus, these in vitro studies documented that transfection of the E2F cis element decoy ODN binds the E2F transcription factor, blocked the induction of cell cycle regulatory gene expression and inhibited VSMC proliferation in a sequence specific manner.

EXAMPLE 2

E2F Decoys In Vivo

Liposomes were prepared as follows: Phosphatidylserine phosphatidylcholine, and cholesterol were mixed in a weight ratio (1:4.8:2) to create a lipid mixture. Lipid was hydrated in a balanced salt solution containing ODN (110 nmol). Purified HVJ(Z) strain was inactivated by UV radiation just before use. The liposome suspension was mixed with HVJ (Z strain) (20,000 hemagglutinating units), incubated, then free HVJ removed by sucrose density gradient centrifugation. The final concentration of encapsulated DNA was calculated as previously reported (Morishita et al. (1993) supra). This method results in a more rapid cellular uptake and nuclear concentration, leading to a 100-fold higher transfection efficiency of ODN than lipofection or passive uptake methods.

The sequences of the phosphorothioate ODN utilized:

```
decoys-1        5'-CTAGATTTCCCGCG-3'      (SEQ ID NO:1)

3'-TAAAGGGCGCCTAG-5'      (SEQ ID NO:2)

mismatched-1    5'-CTAGATTTCGAGCG-3'      (SEQ ID NO:3)

3'-TAAAGCTCGCCTAG-5'      (SEQ ID NO:4)
```

We also examined another set of decoy ODNs containing two binding sites:

```
decoys-2:
5'-GATCAAAAGCGCGAATCAAAAGCGCGAATC-3'  (SEQ ID NO:5)

3'-CTAGTTTTCGCGCTTAGTTTTCGCGCTTAG-5'  (SEQ ID NO:6)

mismatched-1;
5'-GATCAAAGAACTGAATCAAAGAACTGAATC-3'  (SEQ ID NO:7)

3'-CTAGTTTCTTGACTTAGTTTCTTGACTTAG-5'  (SEQ ID NO:8)
```

Rat aortic VSMC (passage 4–10) were studied in a confluent, quiescent state in serum-free media (Morishita et al, J. Clin. Invest. 91, 2580–2585 (1993)). The cells were incubated with hemagglutinating virus Japan (HVJ) liposomes (3 μM) at 4° C. for 5 min and 37° C. for 30 min. Three days after transfection in either calf serum (CS) or serum-free media, cell number was determined by Coulter-Counter (Coulter, Fla.).

EXAMPLE 3

Effect of Decoy ODN on in Vivo Gene Expression

A 2 French Fogarty catheter was used to induce vascular injury in male Sprague-Dawley rats (400–500 g; Charles River Breeding Laboratories) (Hanke et al., *Circ. Res.* 67, 651–659 (1990)). These rats were anesthetized, and a cannula introduced into the left common carotid via the external carotid artery. After vascular injury of the common carotid, the distal injured segment was transiently isolated by temporary ligatures. The HVJ complex was infused into the segment and incubated for 10 min at room temperature. No adverse neurological or vascular effects were observed in any animal undergoing this procedure.

For RNA analysis, vessels were harvested at 6 h, (c-myc and beta-actin) and one day (cdc2 kinase, PCNA and beta-actin) after transfection. RNA was extracted from mismatched or E2F decoy ODN (3 $\mu$M) treated injured or untreated intact vessels by RNAzol (Tel-Test Inc., TX). RT-PCR was performed as described above. For BrdU staining, BrdU was injected into rats (100 mg/kg subcutaneous and 30 mg/kg intraperitoneal at 18 h prior, and then 30 mg/kg intraperitoneal at 12 h prior to sacrifice (Hanke et al., supra)). Rats were sacrificed after day four after transfection. The carotid artery was removed after perfusion-fixation with 4% paraformaldehyde, and processed for immunohistochemistry in a standard manner using anti-BrdU antibodies (Amersham). The proportion of BrdU positive cells was determined by cell counts under light microscopy in a blinded fashion.

Transfection procedures were described above. HVJ-ODN complex (3 $\mu$M) was administered into the rat carotid injured arteries. At two weeks after transfection, rats were sacrificed and vessels were perfusion-fixed with 4% paraformaldehyde. Three individual sections from the middle of transfected segments were analyzed. In addition, three sections from the middle section of the injured untransfected region were also analyzed. Animals were coded so that the operation and analysis were performed without knowledge of which treatment individual animals received. Intimal and medial areas were measured on a digitizing tablet (Southern Micro Instruments, GA). Analysis of variance with subsequent Duncan's test was used to determine significant differences in multiple comparisons. P<0.05 was considered significant.

The scrambled and progesterone responsive element (PRE) decoy sequences utilized as control ODNs are as follows:

```
Scrambled decoys:
5'-TCCAGCTTCGTAGC-3'            (SEQ ID NO:9)

3'-GAAGGATCGATCG-5'             (SEQ ID NO:10)

PRE:
5'-GATCCTGTACAGGATGTTCTAGCTACA-3'  (SEQ ID NO:11)

3'-CTAGGACATGTCCTACAAGATCGATGT-5'  (SEQ ID NO:12)
```

At one day after balloon injury mRNA levels of c-myc, cdc2 and PCNA were elevated in carotid vessels transfected with the control missense E2F element ODN as detected by RT-PCR. However, in vivo transfection of the E2F cis element decoy ODN resulted in a marked decrease in c-myc, cdc2 and PCNA mRNA levels to barely detectable levels similar to uninjured vessels. Moreover, the E2F cis element decoys significantly inhibited bromodeoxyuridine (BrdU) incorporation (a marker of DNA synthesis) within the vessel wall at 4 days post-injury as compared to the missense E2F ODN material. Furthermore, transfection of the E2F decoy ODN (n=8) resulted in a marked suppression of neointima formation at two weeks after angioplasty compared to vessels treated with the HVJ-liposome complex alone (n=5) or mismatched control decoy ODN-treated vessels (n=8). The selectivity of the decoy ODN effect was further confirmed by the fact that the inhibition of the neointima formation was limited to the area of intraluminal transfection (neointima/medial ratio; transfected lesions= 0.291±0.061 vs. untransfected lesions=1.117±0.138, P<0.01). In contrast, the adjacent injured carotid segments outside the area of decoy transfection exhibited neointimal lesions similar to the mismatched ODN-treated control. Moreover, neither transfection of scrambled decoys (14 bp) nor the progesterone response element decoys (27 bp) (Klein-Hitpass et al., *Cell* 60, 247–257 (1990)) resulted in the inhibition of neointima formation.

The specificity of the inhibitory effect of the decoy ODN against E2F on neointima information is supported by several lines of evidence: (1) the two different E2F decoy ODN bind to the E2F transcription factor in a sequence specific manner and transfection of the E2F decoy ODN completely inhibited VSMC proliferation in vitro, whereas the mismatched ODN did not; (2) the in vitro and in vivo experiments documented that the E2F decoy ODN selectively inhibited the expression of the targeted cell cycle regulatory genes (c-myc, PCNA and cdc2 kinase) transactivated by E2F, but not beta-actin (presumably, other E2F transactivated genes such as c-myb might be inhibited); (3) the E2F decoy ODN specifically reduced a quantitative marker of cell cycle progression in vivo (BrdU labeling); (4) the administration of the E2F decoy, but not mismatched, ODN markedly inhibited neointima formation; (5) the prevention of neointima information was limited to the area transfected with the decoy ODN; and (6) neither scrambled nor PRE cis element decoys inhibited the neointima formation.

EXAMPLE 4

Expression of Renin in Cultured Submanibular Gland (SMG) Cell Line

Figure 1A:
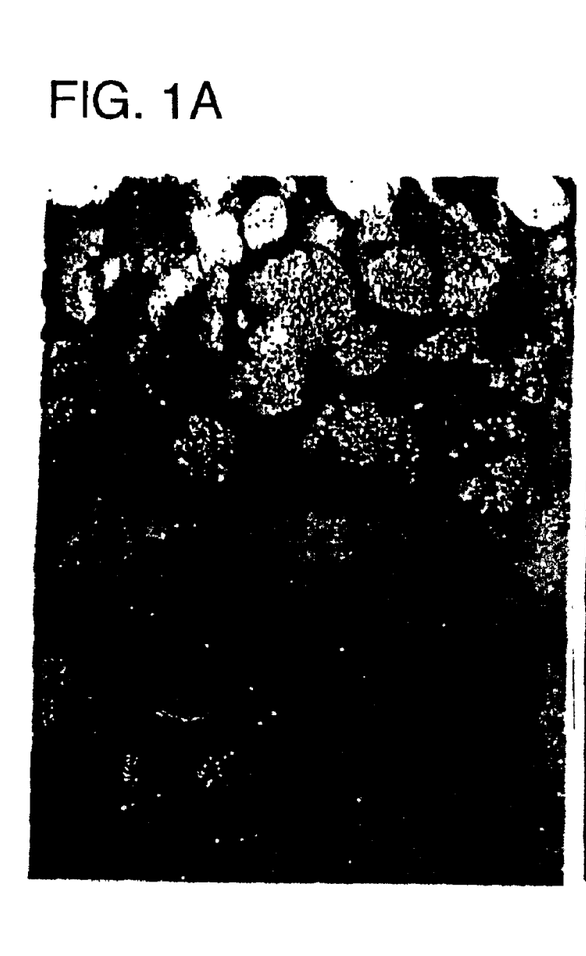
Figure 1B:
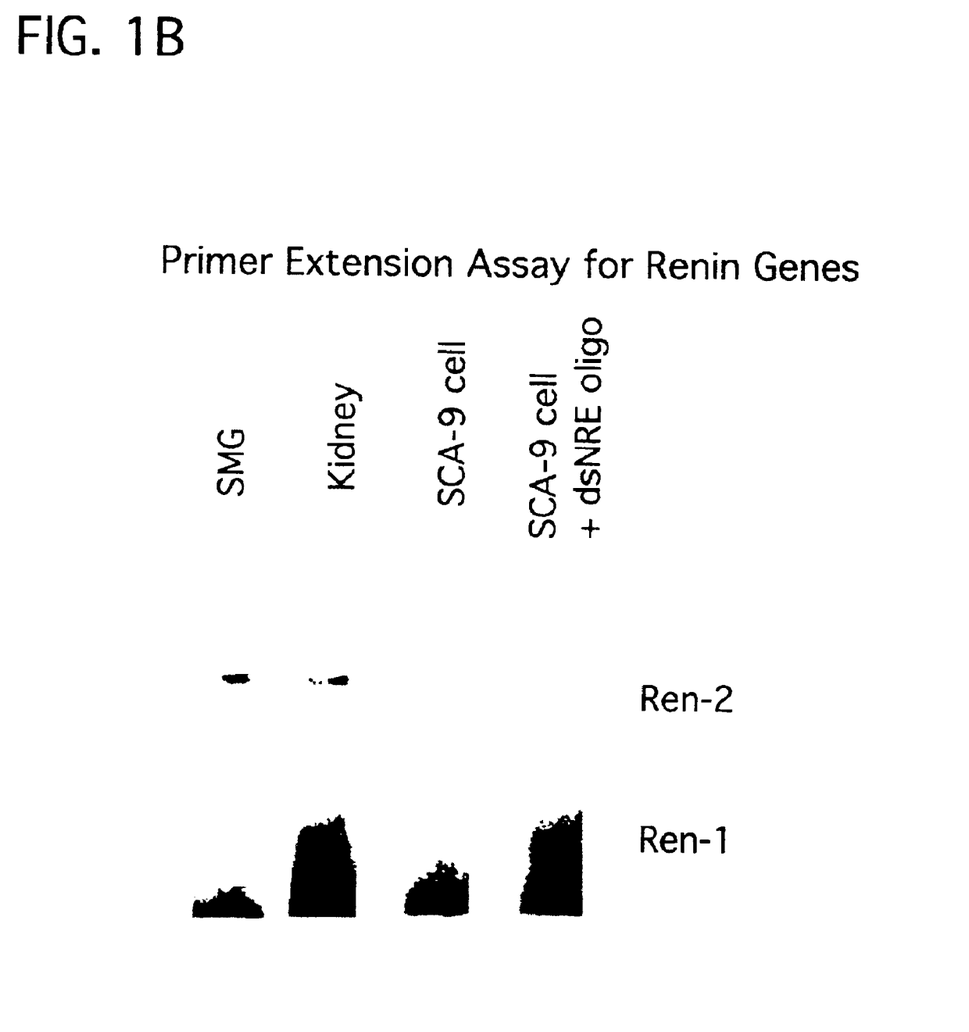
Figure 2:
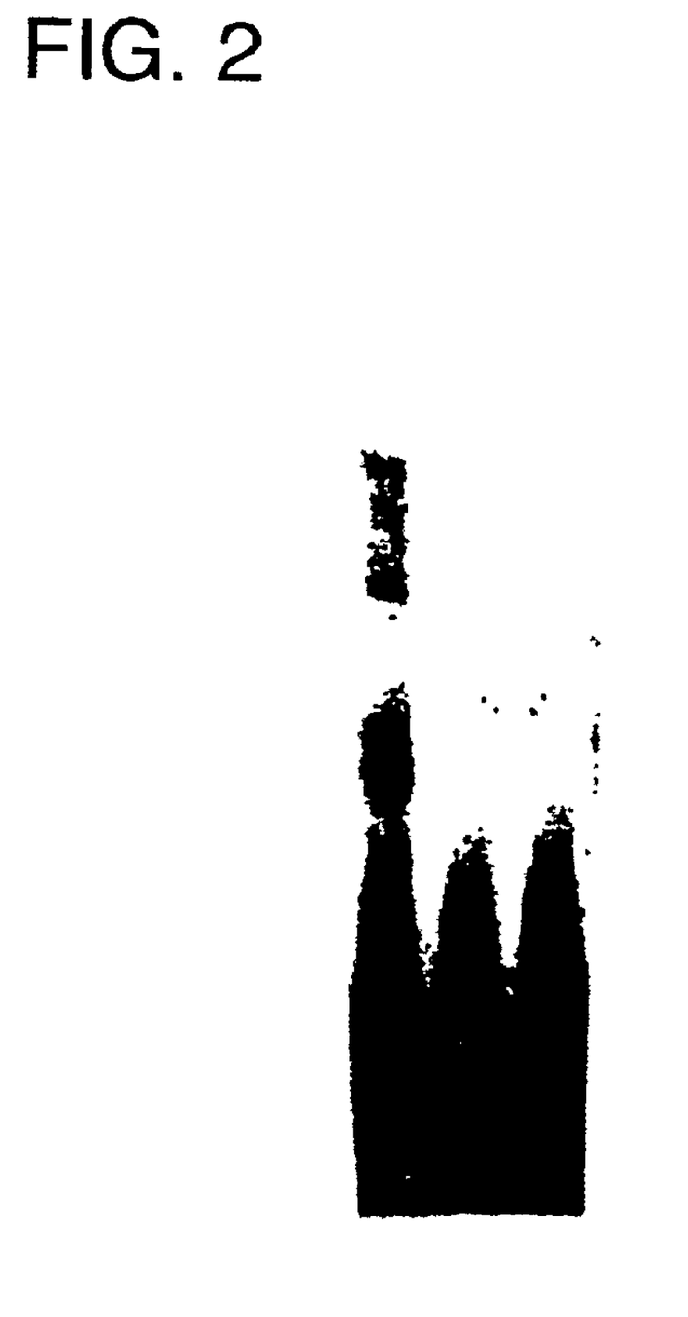

To evaluate the molecular mechanisms which regulate tissue specific renin gene expression, we employed a cell line (SCA-9) derived from a SMG tumor. This line, derived from a two renin gene mouse (Swiss Webster) has been reported to contain renin. Using immunohistochemistry and primer extension analysis, we confirmed that this cell line expresses renin, as shown by immunohistochemistry (FIG. 1A). Moreover, consistent with the SMG origin of this cell line, only the Ren2 gene is transcribed (FIG. 1B). To elucidate the mechanism behind the silencing of the Ren1 gene in this cell line, we examined if the negative response element, NRE, binding protein was present in these cells. Nuclear extracts were prepared from cultured SMG cells and gel mobility shift assay was performed using $^{32}$P-NRE oligonucleotide as a probe (FIG. 2). A specific protein: DNA complex was observed which could be specifically competed with unlabeled NRE oligonucleotide.

These results show that the pattern of renin expression in this cell line is similar to that seen in the SMG in vivo; validating the use of these cells for studies of the mechanism by which renin expression is regulated.

EXAMPLE 5

Use of "Decoy" to Validate the Importance of Cis-Trans Interactions

We examined the feasibility of the "decoy" approach to test whether the NRE:NRE binding protein interaction is responsible for the silencing of the Ren1 gene in the SMG and in the cell line derived from the SMG. This assay is based on the in vivo competition for trans acting factors. The competition is between the endogenous cis elements found in the target gene and exogenously added oligonucleotides corresponding to that cis sequence. This competition will attenuate the authentic cis-trans interaction, result in the removal of the trans factors from the cis element, with the subsequent modulation of gene expression.

Figure 1C:
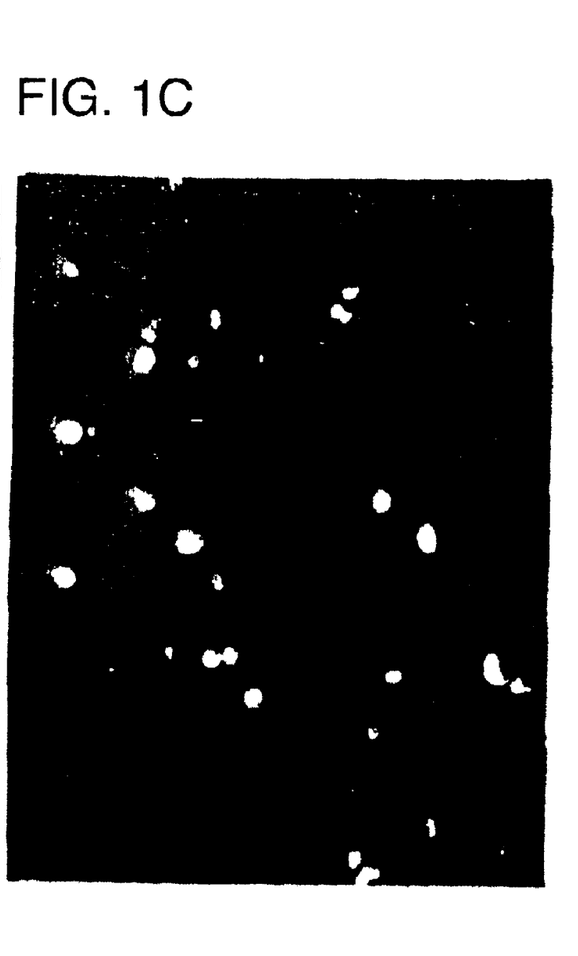

An FITC labeled-double stranded oligonucleotide (33 mer), corresponding to the NRE were introduced into the SMG cell line using the HVJ-liposome technology. The cells were incubated with HVJ-liposome containing NRE decoy at 4° C. for 10 minutes and then at 37° C. for 30 minutes. The cells readily took up the oligomers as evidenced by the intense fluorescent signal which was localized in the nucleus (FIG. 1C). The cells were harvested 24 hours later, RNA was prepared and subjected to the primer extension analysis (FIG. 1B) to examine the expression of the Ren1 and Ren2 genes. Consistent with our hypothesis, introduction of the NRE sequences into these cells resulted in the induction of Ren1 gene expression. The expression of the Ren2 gene was not influenced by the administration of the NRE oligonucleotide.

These results show that NRE:NRE binding protein interaction is responsible for the silencing of Ren1 expression in this cell line and demonstrate the feasibility of using the "decoy" approach to examine the cis-trans interactions responsible for the regulation of renin gene expression.

EXAMPLE 6

In Vivo Gene Transfer into the SMG

Figure 3:
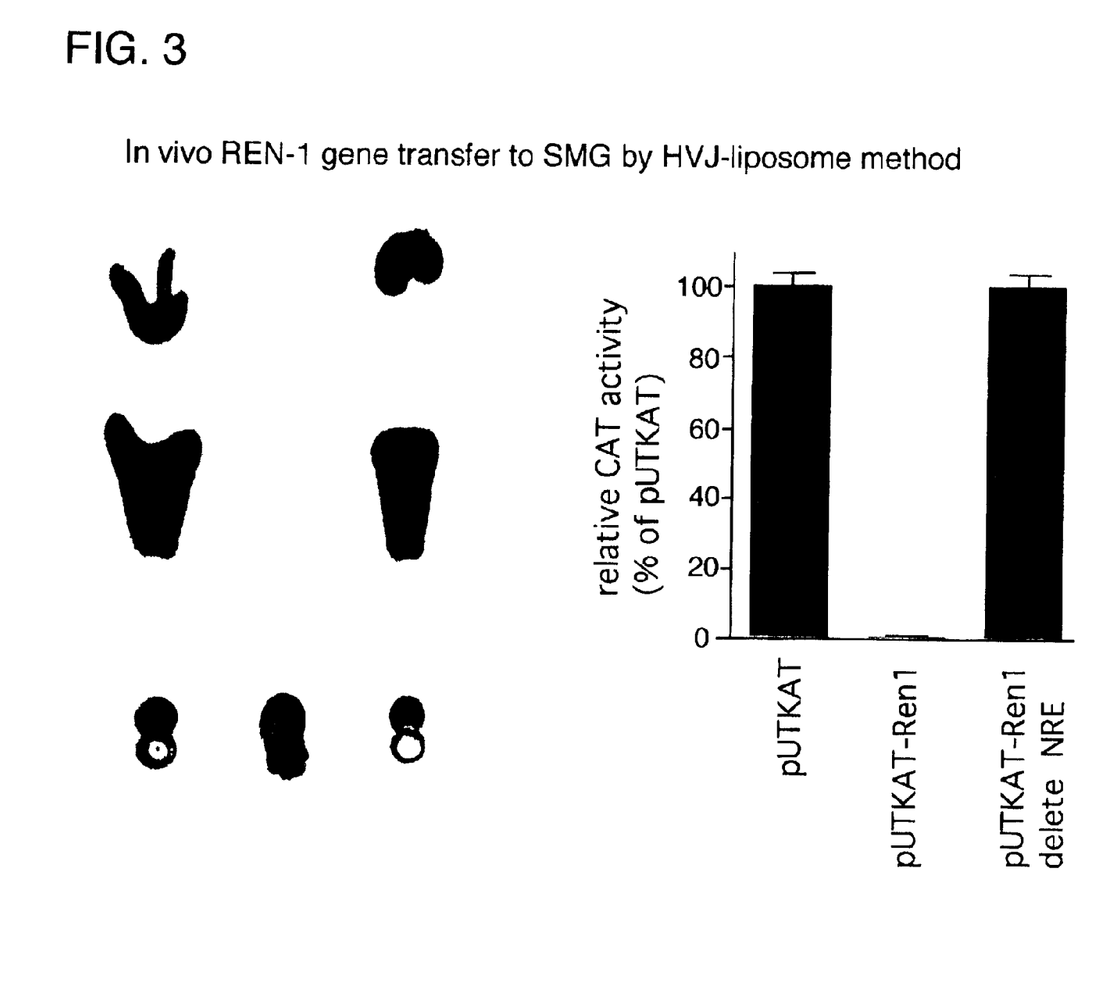
Figure 4:
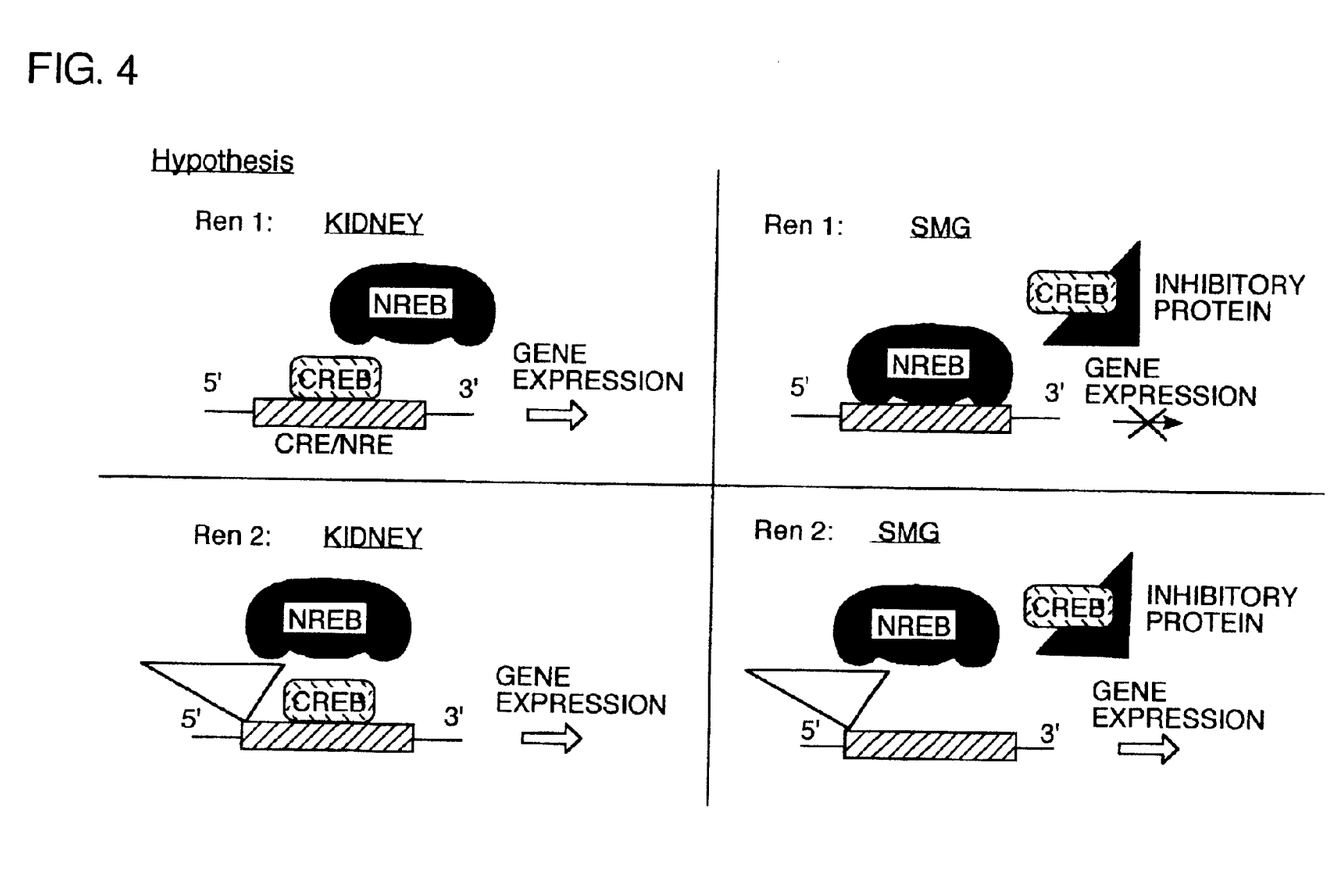

We transfected 10 ug of our expression vectors into the SMG of a DBA/2J mouse using the HVJ-Liposome-DNA complex as describe above. This was accomplished by injecting directly into multiple regions of the gland with a total volume of 100 ul using a 27 gauge needle. Three days after transfection, the SMG was removed, homogenized and the supernatant assayed for CAT activity (FIG. 3). Transfection of pUtk-CAT directed the expression of CAT (Horiuchi et al. (1991) supra). The presence of the Ren1 Xba fragment (containing the CRE/NRE region) decreased CAT expression by approximately 90%. Deletion of the NRE sequence by in vitro mutagenesis resulted in the recovery of CAT expression. These results demonstrate that it is possible to use in vivo gene transfer to examine the expression of genes in the SMG in vivo.

It is evident from the above results, that the subject methods and compositions provide opportunities for preventing injury from acute proliferative diseases or diseases involving expression of proteins, such as proteins associated with cell division, adhesion and/or migration. Thus, the subject methods and compositions can provide safe prophylactic and therapeutic treatments for a number of diseases associated with cellular proliferation and inflammation, resulting in pathogenic conditions.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

---

What is claimed is:

1. A method for inhibiting proliferative lesion formation in a blood vessel, said method comprising introducing into vascular smooth muscle cells of said blood vessel dsDNA that comprises a sequence that is specific for binding to transcription factor E2F; in an amount sufficient to inhibit proliferative lesion formation in said blood vessel.

2. The method of claim 1, wherein said blood vessel is within a mammal.

3. The method of claim 2, wherein said mammal is a human.

4. The method of claim 3, wherein said dsDNA is introduced into said vascular smooth muscle cells of said blood vessel ex vivo.

* * * * *